(12) United States Patent
Lee

(10) Patent No.: US 10,118,551 B1
(45) Date of Patent: Nov. 6, 2018

(54) ANTI-FATIGUE ADJUSTING DEVICE

(71) Applicant: ATake Digital Technology (Shenzhen) Co., Ltd., Shenzhen (CN)

(72) Inventor: Kuo Tsai Lee, Taipei (TW)

( * ) Notice: Subject to any disclaimer, the term of this patent is extended or adjusted under 35 U.S.C. 154(b) by 0 days.

(21) Appl. No.: 15/636,602

(22) Filed: Jun. 28, 2017

(30) Foreign Application Priority Data

Apr. 28, 2017 (CN) .......................... 2017 1 0299302

(51) Int. Cl.
*B60Q 9/00* (2006.01)
(52) U.S. Cl.
CPC ..................... *B60Q 9/00* (2013.01)
(58) Field of Classification Search
CPC ....................................................... B60C 9/00
USPC ........................................................ 340/576
See application file for complete search history.

(56) References Cited

U.S. PATENT DOCUMENTS

| 6,445,303 | B1* | 9/2002 | Aryeh | .................... | G08B 21/06 |
| | | | | | 180/272 |
| 9,058,735 | B2* | 6/2015 | Yang | .................... | A61B 5/1071 |
| 2015/0351690 | A1* | 12/2015 | Toth | .................... | A61B 5/6833 |
| | | | | | 600/373 |

* cited by examiner

*Primary Examiner* — Kerri McNally
(74) *Attorney, Agent, or Firm* — Wayne & King LLC

(57) ABSTRACT

The present disclosure provides an anti-fatigue adjusting device, which includes a wearing housing, a head deflection detecting component, a conductive patch and a controller, the wearing housing is used for wearing on a user's head; the head deflection detecting component includes a gyroscope and an accelerometer, the head deviation detecting component is mounted on the wearing housing, and is using for detecting user's head deflection motion parameter; the conductive patch is used for contacting with user's skin and outputting low frequency pulse current to user, the controller is mounted on the wearing housing, and is electrically connected with the head deflection detecting component and the conductive patch, and is used for acquiring user's head deflection angle, the controller controls the conductive patch to work when the head deflection angle is larger than a preset head deflection angle.

15 Claims, 4 Drawing Sheets

ANTI-FATIGUE ADJUSTING DEVICE

CROSS-REFERENCE TO RELATED APPLICATIONS

This application claims priority to Chinese Patent Application No. 201710299302.7 with a filing date of Apr. 28, 2017. The content of the aforementioned applications, including any intervening amendments thereto, are incorporated herein by reference.

TECHNICAL FIELD

The present disclosure relates to the field of anti-fatigue alarming technologies, and in particular, to an anti-fatigue adjusting device which can be used by driver, other passengers in the car.

BACKGROUND OF THE PRESENT INVENTION

Recently, with the vehicles increasing day by day, the traffic accidents happen frequently. Wherein, the traffic accidents caused for occupant's fatigue account for a large percentage, especially for the driver in the car, when the driver is tried, the traffic accidents will be easily happened, bringing heavy losses to occupants' life and their property.

In view of this situation, a large amount of anti-fatigue products appear on the market, while most of the existing anti-fatigue products can only alert user to know himself/herself fatigue state, and do not have the function of helping user to regain consciousness and correct the fatigue state.

SUMMARY OF PRESENT INVENTION

The main aim of the present disclosure is providing an anti-fatigue adjusting device, which aims to help user to regain consciousness and correct fatigue state.

In order to achieve the above aim, the present disclosure provides an anti-fatigue adjusting device, the anti-fatigue adjusting device includes:

a wearing housing, is used for wearing on a user's head;

a head deflection detecting component, includes a gyroscope and an accelerometer, the head deviation detecting component is mounted on the wearing housing, to be used for detecting the user's head deflection motion parameter;

a conductive patch, is used for contacting with the user's skin and outputting low frequency pulse current to the user when an electric current is applied to the conductive patch; and a controller, is mounted on the wearing housing, and is electrically connected with the head deflection detecting component and the conductive patch, to be used for acquiring the user's head deflection angle according to the head deflection motion parameter, the controller controls the conductive patch to work when the head deflection angle is larger than a preset head deflection angle.

Preferably, the anti-fatigue adjusting device includes a vibrating motor electrically connected with the controller, the controller controls the vibrating motor to work when the head deflection angle is larger than the preset head deflection angle.

Preferably, the anti-fatigue adjusting device further includes a mode selecting key, which is used for selecting the conductive patch and the vibrating motor to work through the controller.

Preferably, the anti-fatigue adjusting device further includes:

a switch key, which is electrically connected with the controller, and is used for controlling the switching of the controller; and an adjusting key, which is electrically connected with the controller, and is used for adjusting a size of the low frequency pulse current outputted by the conductive patch.

Preferably, the anti-fatigue adjusting device further includes a display device, the display device is electrically connected with the controller, the controller controls the display device to display corresponding image according to the size of the low frequency pulse current outputted by the conductive patch.

Preferably, the display device further includes a plurality of LED indicating lamps, the LED indicating lamps are partly mounted in the wearing housing and partly exposed from an external surface of the wearing housing, the controller is electrically connected with the LED indicating lamps, for controlling an amount of the LED indicating lamps which need to work according to the size of the low frequency pulse current outputted by the conductive patch.

Preferably, the wearing housing includes a top cover, and a bottom cover, the top cover and the bottom cover cooperatively form a cavity, the head deflection detecting component and the controller are both received in the cavity, the conductive patch is defined at a lateral surface of the bottom cover.

Preferably, the conductive patch is detachably connected with the bottom cover.

Preferably, the anti-fatigue adjusting device further includes two metal connectors, the metal connectors are connected with the controller and conductive patch, the metal connectors are connected with the bottom cover and the conductive patch.

Preferably, each metal connector includes a connecting part and a holding part connected with the connecting part, the bottom cover defines two through holes, the connecting parts pass through corresponding through holes and are connected with the conductive patch, the holding parts resist on corresponding peripheries of the through holes and are connected with the controller.

Preferably, the conductive patch has two clamping posts, the connecting parts pass through corresponding through holes and are clamped with corresponding clamping posts.

Preferably, each connecting part has a clamping hole, after the connecting parts pass through corresponding through holes, the clamping posts are clamped in corresponding clamping holes.

Preferably, a diameter of each connecting part is smaller than a diameter of each holding part.

Preferably, the anti-fatigue adjusting device further includes a protecting cover, which is coiled around the top cover.

Preferably, the anti-fatigue adjusting device further includes a USB interface, the USB interface is connected with the controller.

Preferably, the anti-fatigue adjusting device further includes a battery, the battery is electrically connected with the controller, the conductive patch and the head deflection detecting component.

The anti-fatigue adjusting device of the present disclosure uses the head deflection detecting component to detect user's head deflection motion parameter, and the controller acquires user's head deflection angle according to the user's head deflection motion parameter, when the head deflection angle is larger than the preset head deflection angle, the controller controls the conductive patch to output low frequency pulse current to stimulate user's skin, therefore, user can regain consciousness due to the stimulation of the low frequency pulse current, for achieving the effect of correcting fatigue state.

DESCRIPTION OF THE DRAWINGS

To illustrate the technical solutions according to the embodiments of the present invention or in the prior art more dearly, the accompanying drawings for describing the embodiments or the prior art are introduced briefly in the following. Apparently, the accompanying drawings in the following description are only about some embodiments of the present invention, and persons of ordinary skill in the art can derive other drawings from the accompanying drawings without creative efforts.

Labels illustration for drawings.

Figure 1:
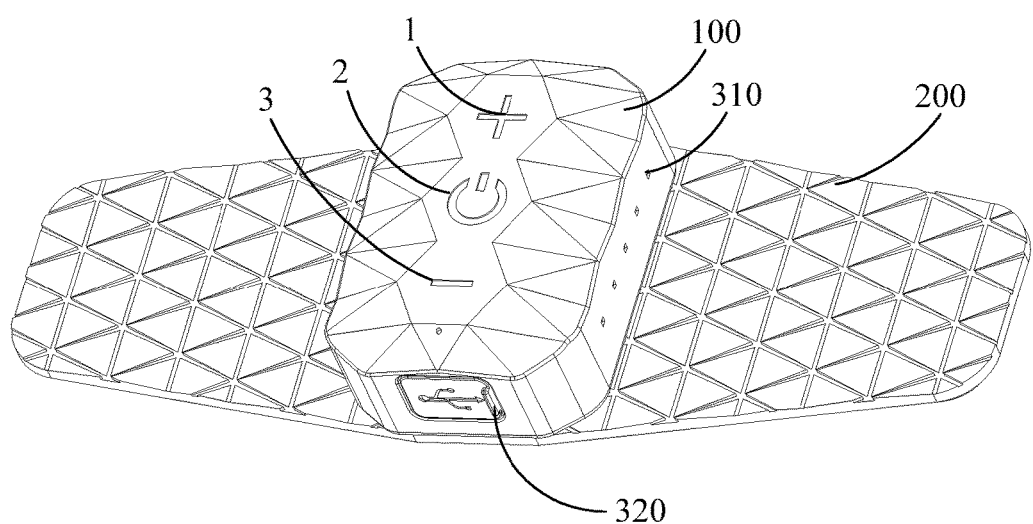
FIG. 1 is a structure diagram of an anti-fatigue adjusting device provided by an exemplary embodiment of the present disclosure.

| Label | Name |
| --- | --- |
| 100 | wearing housing |
| 110 | to cover |
| 120 | bottom cover |
| 121 | mounting hole |
| 122 | through hole |
| 130 | protecting cover |
| 200 | conductive patch |
| 210 | conductive film |
| 211 | clamping post |
| 220 | mercury glue |
| 300 | controller |
| 310 | LED inclicatin lam |
| 320 | USB interface |
| 400 | vibrating motor |
| 500 | battery |
| 700 | metal connector |
| 1 | switch key |
| 2 | increasing key |
| 3 | reducing key |

The realizing of the aim, functional characteristics, advantages of the present disclosure are further described in detail with reference to the accompanying drawings and the embodiments.

DETAILED DESCRIPTION OF PREFERRED EMBODIMENTS

The technical solutions of the embodiments of the present disclosure will be clearly and completely described in the following with reference to the accompanying drawings. It is obvious that the embodiments to be described are only a part rather than all of the embodiments of the present invention. All other embodiments obtained by persons skilled in the art based on the embodiments of the present invention without creative efforts shall fall within the protection scope of the present invention.

It is to be understood that, all the directional instructions of in the present disclosure (such as top, down, left, right, front, back . . . ) can only be used for explaining relative position relations, moving condition of the elements under a special form (referring to figures), and so on, if the special form changes, the directional instructions changes accordingly.

In addition, the descriptions, such as the "first", the "second" in the present disclosure, can only be used for describing the aim of description, and cannot be understood as indicating or suggesting relative importance or impliedly indicating the number of the indicated technical character.

Therefore, the character indicated by the "first", the "second" can express or impliedly include at least one character. In addition, the technical proposal of each exemplary embodiment can be combined with each other, however the technical proposal must base on that the ordinary skill in that art can realize the technical proposal, when the combination of the technical proposals occurs contradiction or cannot realize, it should consider that the combination of the technical proposals does not existed, and is not contained in the protection scope required by the present disclosure.

When a user is in a non-fatigue state, the head of the user is normally in a vertical state; when the user is in a fatigue state, the head of the user will unconsciously deflect from the vertical direction, therefore forming a deflection angle between the head of the user and the vertical direction, so that whether the user is in the fatigue state can be determined through detecting the deflection angle between the head of the user and the vertical direction, for helping user to correct the fatigue state.

Therefore, the present disclosure provides an anti-fatigue adjusting device, which can detect the deflection angle between the head of the user and the vertical direction, and stimulate the user's skin according to the degree of the deflection angle, for helping the user to regain consciousness, and correct the fatigue state. It is to be noted that, the anti-fatigue adjusting device can be available for a driver or other passengers in a car to prevent fatigue, or for people who work or study to correct working, reading posture.

Referring to FIGS. 1-4, the anti-fatigue adjusting device of the present disclosure, includes a wearing housing 100, a head deflection detecting component (not shown), a conductive patch 200 and a controller 300, wherein, the wearing housing 100 is used for wearing on a user's head; the head deflection detecting component (not shown) includes a gyroscope and an accelerometer, the head deviation detecting component is mounted on the wearing housing 100, and to be used for detecting the user's head deflection motion parameter; the conductive patch 200 is used for contacting with the user's skin and outputting low frequency pulse current to the user when an electric current is applied; and the controller 300 is mounted on the wearing housing 100, and is electrically connected with the head deflection detecting component and the conductive patch 200, and to be used for acquiring the user's head deflection angle according to the head deflection motion parameter, the controller 300 controls the conductive patch 200 to work when the head deflection angle is larger than a preset head deflection angle.

In an exemplary embodiment, when the anti-fatigue adjusting device works, the head deflection detecting component can real time detect the user's head deflection motion parameter, and send the head deflection motion parameter to the controller 300, the controller 300 acquires the user's head deflection angle according to the head deflection motion parameter, and compares the head deflection angle with the preset head deflection angle, when the head deflection angle is larger than the preset head deflection angle, the controller 300 controls the conductive patch 200 to output pulse current to stimulate the user's skin.

The head deflection detecting component is integrated on the controller 300, the technology of that the controller 300 acquires the head deflection angle according to the head deflection motion parameter detected by the head deflection detecting component is an existing technology, wherein, the gyroscope of the head deflection detecting component is used for detecting an angular rate of the user's head defecting from the vertical direction; the accelerometer of the head deflection detecting component is used for detecting an acceleration value of the user's head defecting from the vertical direction, the controller 300 acquires the head deflection angle through periodically reading the deflection motion parameter detected by the gyroscope and the accelerometer, and according to a fusion algorithm of the gyroscope and the accelerometer, the detail is no need to repeated again; obviously, the detecting principle of the head deflection detecting component leads us to know that the head deflection detecting component can detect user's head deflection motion parameter, no matter which position of the head the wearing housing 100 of the anti-fatigue adjusting device is worn on, considering stability and comfort of wearing the wearing housing on head, the wearing housing 100 can be preferably worn on user's neck.

The controller 300 defines a preset head deflection angle, the controller 300 real time detect the head deflection motion parameter according to the head deflection detecting component, for acquiring the head deflection angle, when the head deflection angle is larger than a preset head deflection angle, the controller 300 controls the conductive patch 200 to output low frequency pulse current; when the head deflection angle is not larger than a preset head deflection angle, the controller 300 controls the conductive patch 200 to stop outputting low frequency pulse current; the low frequency pulse current can stimulate and treat user's physical fatigue, especially excite neuromuscular tissues and ease pain; user's skin can produce twitch due to the stimulating of the low frequency pulse current, for stimulating the energy of the muscle tissue, and user can remove fatigue, and regain consciousness.

Figure 2:
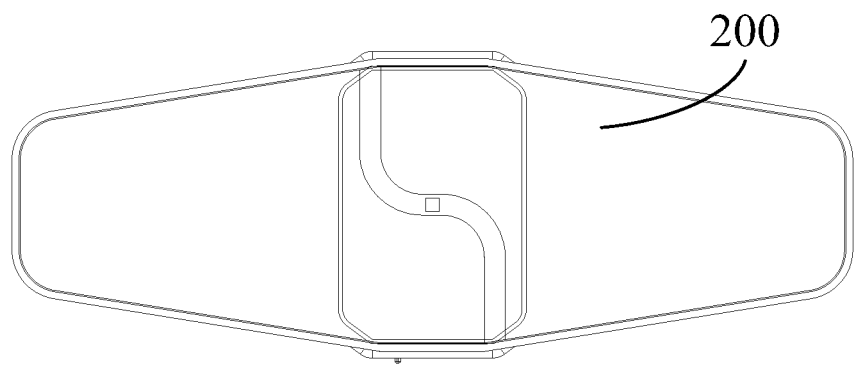
FIG. 2 is an upward view of the anti-fatigue adjusting device shown in FIG. 1.
Figure 4:
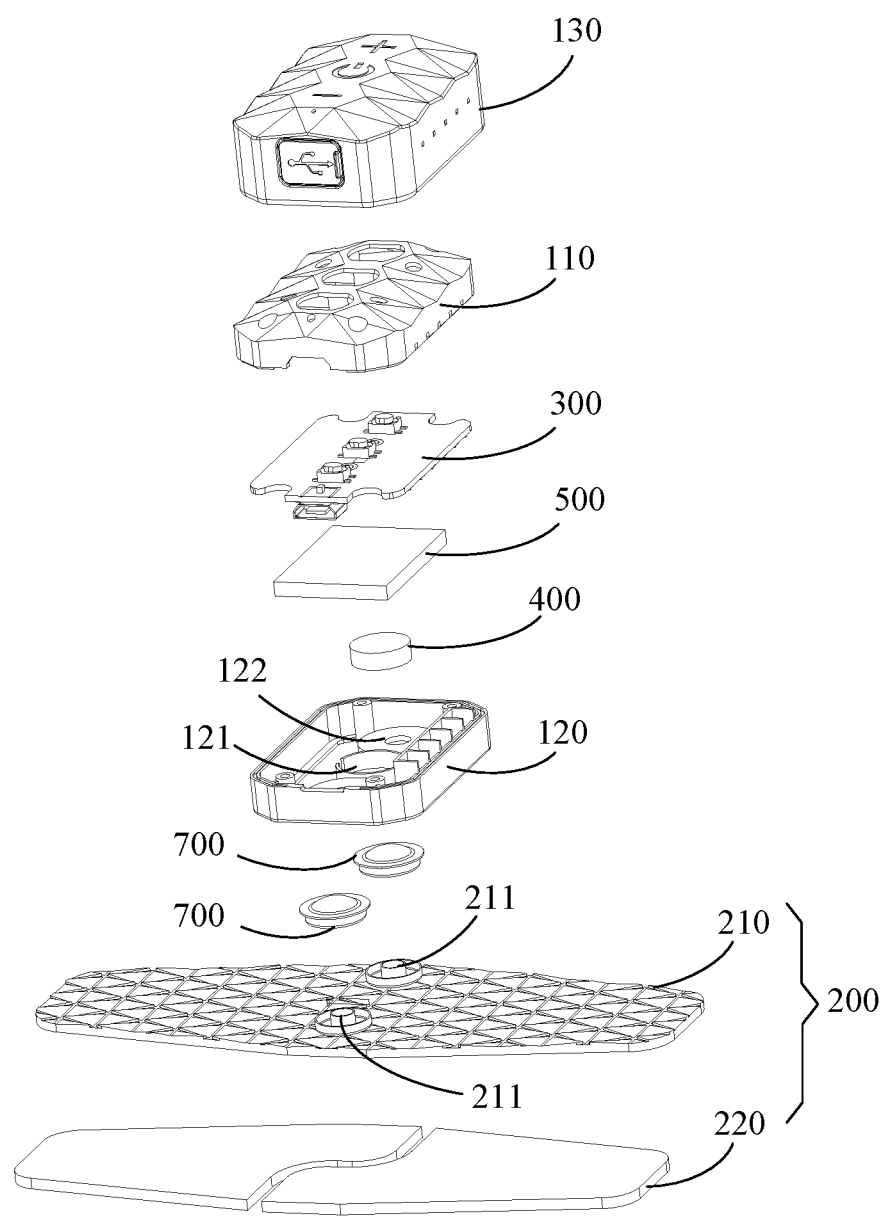
FIG. 4 is an exploded diagram of the anti-fatigue adjusting device shown in FIG. 1.

Referring to FIG. 2 and FIG. 4, the conductive patch 200 is used for outputting pulse current to user, the material of the conductive patch 200 is conductive material, such as an electrode plate or a conductive silicone patch. In detail, the conductive patch 200 includes a mercury glue 220 and a silicone conductive film 210 located at the mercury glue 220; the conductive film 210 is electrically connected with the controller 300; the mercury glue 220 has good conductivity, bonding capacity and flexibility, can be used for directly outputting low frequency pulse current to user when the mercury glue 220 is pasted on user's skin.

The anti-fatigue adjusting device of the present disclosure uses the head deflection detecting component to detect user's head deflection motion parameter, and the controller 300 acquires user's head deflection angle according to the user's head deflection motion parameter, when the head deflection angle is larger than the preset head deflection angle, the controller 300 controls the conductive patch 200 to output low frequency pulse current to stimulate user's skin, therefore user can regain consciousness due to the stimulation of the low frequency pulse current, for achieving the effect of correcting fatigue state.

It is to be noted that, the wearing manner of the wearing housing 100 is not limited, the wearing housing 100 can have a wearing clip, for clipping the wearing housing 100 on neck, or the wearing housing 100 can be pasted on user's neck through the conductive patch 200. Preferably, the wearing housing 100 includes a top cover 110, and a bottom cover 120, the top cover 110 and the bottom cover 120 cooperatively form a cavity, the head deflection detecting component and the controller 300 are both received in the cavity, the conductive patch 200 is located at a lateral surface of the bottom cover 120. When wearing the anti-fatigue adjusting device, user can directly paste the conductive patch 200 on the neck, the wearing manner is easy.

The material of the wearing housing 100 is preferable light weight, low cost, such as, a resin, so that the cost of the wearing housing is low, and the resin has the property of thin and light, therefore, the wearing housing 100 is much lighter and easier to wear, and is not easy to bring a load to user's neck. In order to avoid the dust entering into a gap between the top cover 110 and the bottom cover 120, the wearing housing 100 further includes a protective cover 130 coiled around an external surface of the top cover 110.

Furthermore, in order to improve the alarm warning effect of the anti-fatigue adjusting device, the anti-fatigue adjusting device includes a vibrating motor 400 electrically connected with the controller 300, the controller 300 controls the vibrating motor 400 to work when the head deflection angle is larger than a preset head deflection angle.

In an exemplary embodiment, a bottom surface of the bottom cover 120 has a mounting hole 121 which is used for mounting the vibrating motor 400, the vibrating motor 400 works to produce vibration which can flap and massage user's neck, so that the alarm warning effect can be improved. The vibrating motor 400 and the conductive patch 200 can work asynchronously, or synchronously, which can be set according to user's need.

Preferably, the anti-fatigue adjusting device includes a mode selecting key (not shown), which is used for selecting the conductive patch 200 and the vibrating motor 400 to work through the controller 300.

In an exemplary embodiment, user can select the working mode of the anti-fatigue adjusting device through the mode selecting key, such as, the mode selecting key has an alarming mode and a correcting mode, when the anti-fatigue adjusting device boots, the vibrating motor 400 and the conductive patch 200 synchronously work by default; when the alarming mode is selected, the controller 300 controls the vibrating motor 400 to work, the vibrating motor 400 vibrates and flaps user; when the correcting mode is selected, the controller 300 controls the conductive patch 200 to work, the conductive patch 200 outputs the low frequency pulse current to stimulate the user.

Furthermore, the anti-fatigue adjusting device further includes a switch key 1 and an adjusting key, wherein, the switch key 1 is electrically connected with the controller 300, and is used for controlling the switching of the controller 300; the adjusting key is electrically connected with the controller 300, and is used for adjusting a size of the low frequency pulse current outputted by the conductive patch 200.

In detail, the adjusting key includes an increasing key 2 and a reducing key 3, the adjusting key has five grades of low frequency pulse current, therefore user can adjust the size of the low frequency pulse current outputted by the conductive patch 200 according to user's tolerance of the low frequency pulse current, for meeting different user's need.

The mode selecting key, the switch key 1 and the adjusting key are all exposed from the protective cover 130. Of course, the control mode of the anti-fatigue adjusting device of the present disclosure is not limited to such embodiments, the anti-fatigue adjusting device can also be controlled by a wireless remote controller, the control mode through the wireless remote controller is easier to be operated.

Furthermore, the anti-fatigue adjusting device further includes a display device, the display device is electrically connected with the controller 300, the controller 300 controls the display device to display corresponding image according to the size of the low frequency pulse current outputted by the conductive patch 200.

In an exemplary embodiment, the display device displays the image, when user adjusts the size of the low frequency pulse current outputted by the conductive patch 200, user can know the size of the low frequency pulse current outputted by the conductive patch 200 through the image displayed in the display device; wherein, the display device can be display screen or indicating lamp, there is no specific requirement; the image can be detail data of the low frequency pulse current, or colors corresponding to the size of the low frequency pulse current, or the amounting of the indicating lamps which are working.

Figure 3:
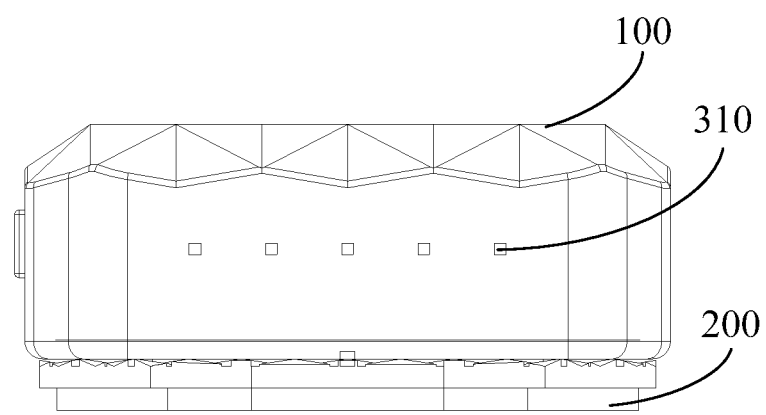
FIG. 3 is a right view of the anti-fatigue adjusting device shown in FIG. 1.

Referring to FIG. 1 and FIG. 3, preferably, the display device includes a plurality of LED indicating lamps 310, the LED indicating lamps 310 are partly mounted in the wearing housing 100 and partly exposed from an external surface of the wearing housing 100, the controller 300 is electrically connected with the LED indicating lamps 310, for controlling the amount of the LED indicating lamps 310 which need to work according to the size of the low frequency pulse current outputted by the conductive patch 200, therefore, user can know the size of the low frequency pulse current outputted by the conductive patch 200 by checking the amount of the LED indicating lamps 310 which are working.

In detail, a number of the LED indicating lamps 310 can be five, these five LED indicating lamps 310 are separately located at a side of the controller 300, the top cover 110 and the protecting cover 130 both define a perspective area corresponding to the LED indicating lamps 310. The five LED indicating lamps 310 correspond to five grades of low frequency pulse current, respectively, such as, when a value of the low frequency pulse current corresponds to a value of a first frequency pulse current, one LED indicating lamp 310 located at an edge of the five LED indicating lamps 310 works; when the value of the low frequency pulse current corresponds to a value of a second frequency pulse current, two adjacent LED indicating lamps 310 located at the edge of the five LED indicating lamps 310 work.

Furthermore, the anti-fatigue adjusting device further includes a battery 500, the battery 500 is electrically connected with the controller 300, the conductive patch 200 and the head deflection detecting component, and provides power to the controller 300, the conductive patch 200 and the head deflection detecting component.

Furthermore, the anti-fatigue adjusting device further has a USB interface 320, the USB interface 320 is electrically connected with the controller 300, and can be used for providing power to the controller 300, and the battery 500 electrically connected with a control circuit of the controller 300, or transmitting data for user.

In an exemplary embodiment, in order to avoid that the USB interface 320 is damages due to damp or dust, a dust-proof cover is provided to cover the USB interface 320, for avoiding damp or dust entering into the USB interface 320.

Furthermore, the conductive patch 200 is detachably connected with the bottom cover 120, the anti-fatigue adjusting device can be repaired or maintained by dismounting the conductive patch 200 from the bottom cover 120.

Furthermore, the anti-fatigue adjusting device further includes two metal connectors 700, the metal connectors 700 are connected with the controller 300 and conductive patch 200, the metal connectors are clamped with the bottom cover 120 and the conductive patch 200.

In detail, each metal connector 700 includes a connecting part and a holding part connected with the connecting part, each connecting part has a clamping hole, the bottom cover 120 defines two through holes 122, the conductive film 210 has two clamping posts 211 corresponding to the clamping holes of the connecting parts, the connecting parts are connected with the anode and the cathode of the control circuit of the controller 300, respectively. The connecting parts pass through corresponding through holes 122, and the clamping posts 211 are received in corresponding clamping holes, the holding parts resist on corresponding peripheries of the through holes 122 and are connected with the controller 300. It is to be noted that, a diameter of each connecting part is smaller than a diameter of each holding part.

In an exemplary embodiment, on one side, the metal connectors 700 can be used for connecting the conductive patch 200 with the bottom cover 120, so that the conductive patch 200 is not easy to fall; on the other side, the metal connectors 200 can be used for realizing that the conductive patch 200 can be electrically connected with the control circuit of the controller 300.

The embodiments above are preferably embodiments of the present disclosure, and the present disclosure is not limited to such embodiments, equivalent structure conversion based on the specification and the drawing of the present disclosure, or directly or indirectly used in other related technical field, both similarly within the protection scope of the present disclosure.

I claim:

1. An anti-fatigue adjusting device, comprising:
   a wearing housing (100), being used for wearing on a user's head, the wearing housing (100) comprising a bottom cover (120);
   a head deflection detecting component, comprising a gyroscope and an accelerometer, the head deviation detecting component being mounted on the wearing housing (100), to be used for detecting the user's head deflection motion parameter;
   a conductive patch (200), being used for contacting with the user's skin and outputting low frequency pulse current to the user when an electric current being applied to the conductive patch (200), the conductive patch (200) being defined at a lateral surface of the bottom cover and detachably connected with the bottom cover (120); and
   a controller (300), being mounted on the wearing housing (100), and being electrically connected with the head deflection detecting component and the conductive patch (200), to be used for acquiring the user's head deflection angle according to the head deflection motion parameter, the controller (300) controlling the conductive patch (200) to work when the head deflection angle being larger than a preset head deflection angle.

2. The anti-fatigue adjusting device according to claim 1, wherein the anti-fatigue adjusting device comprises a vibrating motor (400) electrically connected with the controller (300) the controller (300) controls the vibrating motor (400) to work when the head deflection angle is larger than the preset head deflection angle.

3. The anti-fatigue adjusting device according to claim 2, wherein the anti-fatigue adjusting device further comprises a mode selecting key, which is used for selecting the conductive patch (200) and the vibrating motor (400) to work through the controller (300).

4. The anti-fatigue adjusting device according to claim 1, wherein the anti-fatigue adjusting device further comprises:
- a switch key 1, which is electrically connected with the controller (300), and is used for controlling the switching of the controller (300); and
- an adjusting key, which is electrically connected with the controller (300), and is used for adjusting a size of the low frequency pulse current outputted by the conductive patch (200).

5. The anti-fatigue adjusting device according to claim 4, wherein the anti-fatigue adjusting device further comprises a display device, the display device is electrically connected with the controller (300), the controller (300) controls the display device to display corresponding image according to the size of the low frequency pulse current outputted by the conductive patch (200).

6. The anti-fatigue adjusting device according to claim 5, wherein the display device further comprises a plurality of LED indicating lamps (310), the LED indicating lamps (310) are partly mounted in the wearing housing (100) and partly exposed from an external surface of the wearing housing (100), the controller (300) is electrically connected with the LED indicating lamps (310), for controlling an amount of the LED indicating lamps (310) which need to work according to the size of the low frequency pulse current outputted by the conductive patch (200).

7. The anti-fatigue adjusting device according to claim 1, wherein the wearing housing (100) comprises a top cover (110), the top cover and the bottom cover cooperatively form a cavity, the head deflection detecting component and the controller are both received in the cavity.

8. The anti-fatigue adjusting device according to claim 7, wherein the anti-fatigue adjusting device further comprises two metal connectors (700), the metal connectors (700) are connected with the controller (300) and conductive patch (200), the metal connectors are connected with the bottom cover (120) and the conductive patch (200).

9. The anti-fatigue adjusting device according to claim 8, wherein each metal connector (700) comprises a connecting part and a holding part connected with the connecting part, the bottom cover (120) defines two through holes (122), the connecting parts pass through corresponding through holes (122) and are connected with the conductive patch (200), the holding parts resist on corresponding peripheries of the through holes (122) and are connected with the controller (300).

10. The anti-fatigue adjusting device according to claim 9, wherein the conductive patch (200) has two clamping posts (211), the connecting parts pass through corresponding through holes (122) and are clamped with corresponding clamping posts (211).

11. The anti-fatigue adjusting device according to claim 10, wherein each connecting part has a clamping hole, after the connecting parts pass through corresponding through holes (122), the clamping posts (211) are clamped in corresponding clamping holes.

12. The anti-fatigue adjusting device according to claim 9, wherein a diameter of each connecting part is smaller than a diameter of each holding part.

13. The anti-fatigue adjusting device according to claim 7, wherein the anti-fatigue adjusting device further comprises a protecting cover (130), which is coiled around the top cover (110).

14. The anti-fatigue adjusting device according to claim 1, wherein the anti-fatigue adjusting device further comprises a USB interface (320), the USB interface is connected with the controller (300).

15. The anti-fatigue adjusting device according to claim 1, wherein the anti-fatigue adjusting device further comprises a battery (500), the battery (500) is electrically connected with the controller (300), the conductive patch (200) and the head deflection detecting component.

\* \* \* \* \*